United States Patent
Dmuschewsky

(10) Patent No.: US 11,583,404 B2
(45) Date of Patent: Feb. 21, 2023

(54) INTERMEDIATE SEGMENT FOR A JOINT COMPONENT

(71) Applicant: Waldemar Link GmbH & Co. KG, Hamburg (DE)

(72) Inventor: Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 703 days.

(21) Appl. No.: 16/463,800

(22) PCT Filed: Nov. 15, 2017

(86) PCT No.: PCT/EP2017/079301
§ 371 (c)(1),
(2) Date: May 23, 2019

(87) PCT Pub. No.: WO2018/095778
PCT Pub. Date: May 31, 2018

(65) Prior Publication Data
US 2021/0378829 A1 Dec. 9, 2021

(30) Foreign Application Priority Data
Nov. 24, 2016 (DE) .................... 10 2016 223 289.4

(51) Int. Cl.
*A61F 2/38* (2006.01)
*A61F 2/30* (2006.01)
*A61B 34/10* (2016.01)

(52) U.S. Cl.
CPC ........ *A61F 2/30734* (2013.01); *A61F 2/3859* (2013.01); *A61F 2002/30112* (2013.01);
(Continued)

(58) Field of Classification Search
None
See application file for complete search history.

(56) References Cited

U.S. PATENT DOCUMENTS 4,936,847 A * 6/1990 Manginelli ........... A61F 2/3859
623/20.16
5,549,685 A * 8/1996 Hayes .................. A61F 2/3859
623/20.16
(Continued)

FOREIGN PATENT DOCUMENTS

DE 693 22 508 T2 7/1999
EP 0850608 A2 * 12/1997
(Continued)

OTHER PUBLICATIONS

International Search Report and Written Opinion dated Jul. 24, 2018 in corresponding International Application No. PCT/EP2017/079301.
(Continued)

*Primary Examiner* — Ann Schillinger
(74) *Attorney, Agent, or Firm* — Chiesa, Shahinian & Giantomasi PC

(57) ABSTRACT

The present invention discloses an intermediate segment (20) for arrangement between a concave implantation surface (14) of a joint component (10), particularly a femoral prosthesis, and bone tissue. The intermediate segment (20) comprises an intermediate segment body (23) with at least one side (24, 25) facing the joint component (10), wherein one (24) of the at least one side facing the joint component is convex. In addition, the intermediate segment (20) comprises a locking mechanism for attaching the intermediate segment to the joint component with at least a first (21) and a second (32) latching element, wherein at least one of the latching elements (21, 32) is movable. The present invention also relates to a joint component (10) comprising an intermediate segment (20) and a method for securing an intermediate segment (20) to a joint component (10).

19 Claims, 2 Drawing Sheets

(52) U.S. Cl.
CPC ............... *A61F 2002/30492* (2013.01); *A61F 2002/30736* (2013.01)

(56) References Cited

U.S. PATENT DOCUMENTS

| | | | | |
|---|---|---|---|---|
| 5,571,194 | A * | 11/1996 | Gabriel | A61F 2/3859 623/20.16 |
| 5,683,472 | A | 11/1997 | O'Neil et al. | |
| 5,776,201 | A * | 7/1998 | Colleran | A61F 2/4684 606/88 |
| 5,984,969 | A * | 11/1999 | Matthews | A61F 2/3859 623/20.11 |
| 6,004,352 | A * | 12/1999 | Buni | A61F 2/389 623/20.33 |
| 6,005,018 | A * | 12/1999 | Cicierega | A61F 2/30734 623/20.16 |
| 8,632,599 | B1 * | 1/2014 | Bonitati | A61F 2/3859 623/20.16 |
| 10,258,477 | B2 * | 4/2019 | Jordan | A61F 2/389 |
| 10,702,399 | B2 * | 7/2020 | Jordan | A61F 2/3886 |
| 2005/0075736 | A1 * | 4/2005 | Collazo | A61F 2/4684 623/20.16 |
| 2010/0179661 | A1 * | 7/2010 | Berelsman | A61F 2/38 623/20.11 |
| 2014/0081408 | A1 * | 3/2014 | Lieberman | A61F 2/3836 623/20.15 |
| 2015/0335438 | A1 | 11/2015 | Pierce et al. | |

FOREIGN PATENT DOCUMENTS

| | | |
|---|---|---|
| EP | 0 850 606 A2 | 7/1998 |
| EP | 0 850 608 A2 | 7/1998 |
| RU | 2 110 972 C1 | 5/1998 |
| RU | 2 114 580 C1 | 7/1998 |
| RU | 2 127 096 C1 | 3/1999 |

OTHER PUBLICATIONS

Search Report issued in the corresponding Russian Application No. RU 2019119205.
Search Report issued in the corresponding German Priority Application No. DE 10 2016 223 289.4.

* cited by examiner

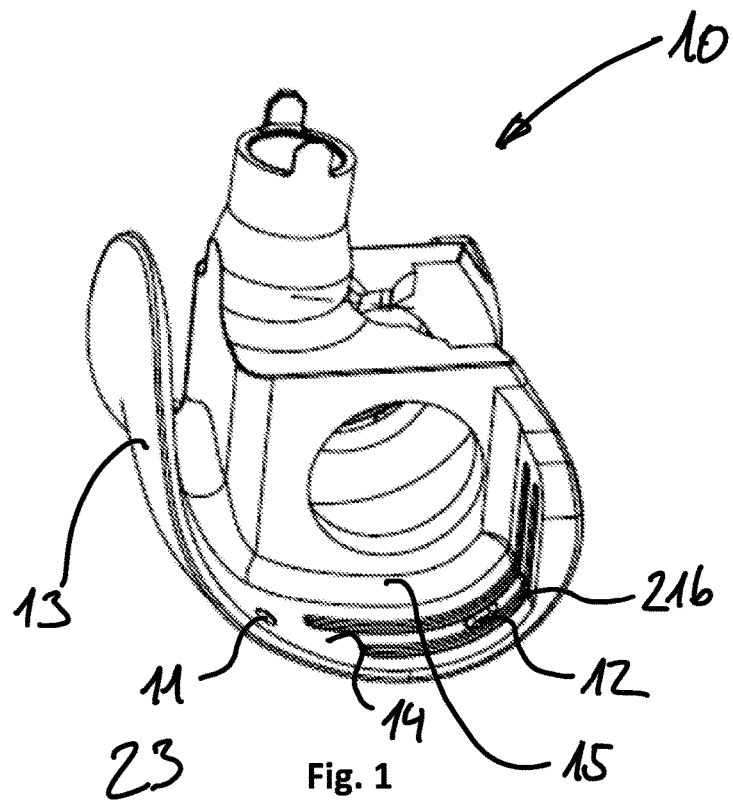
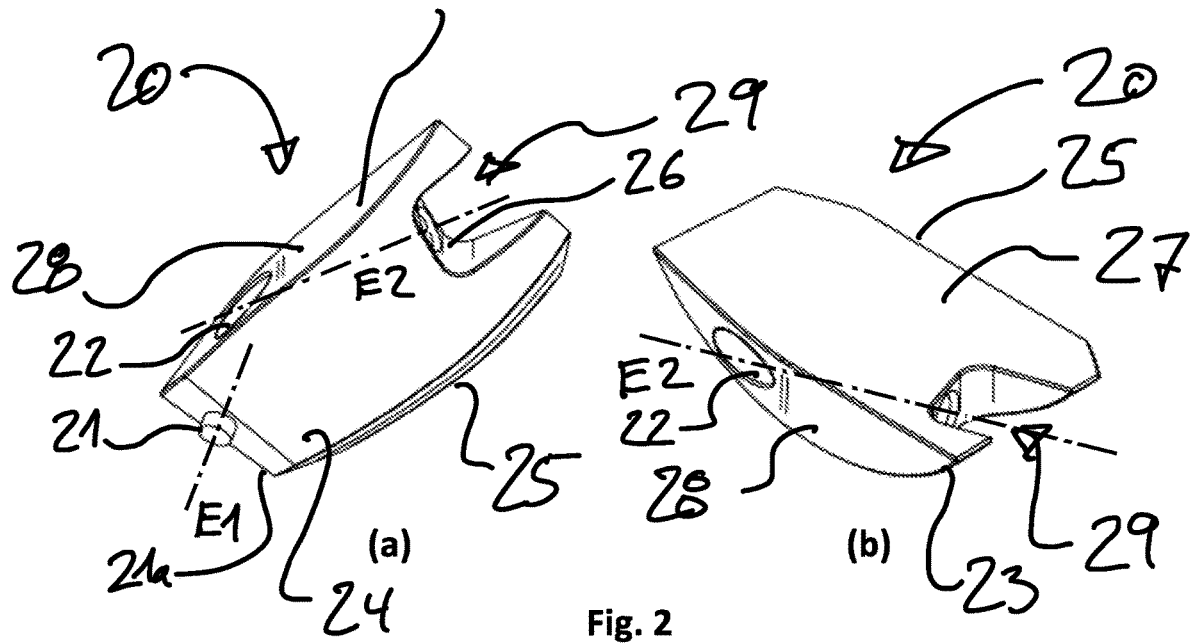
Fig. 1
Fig. 2

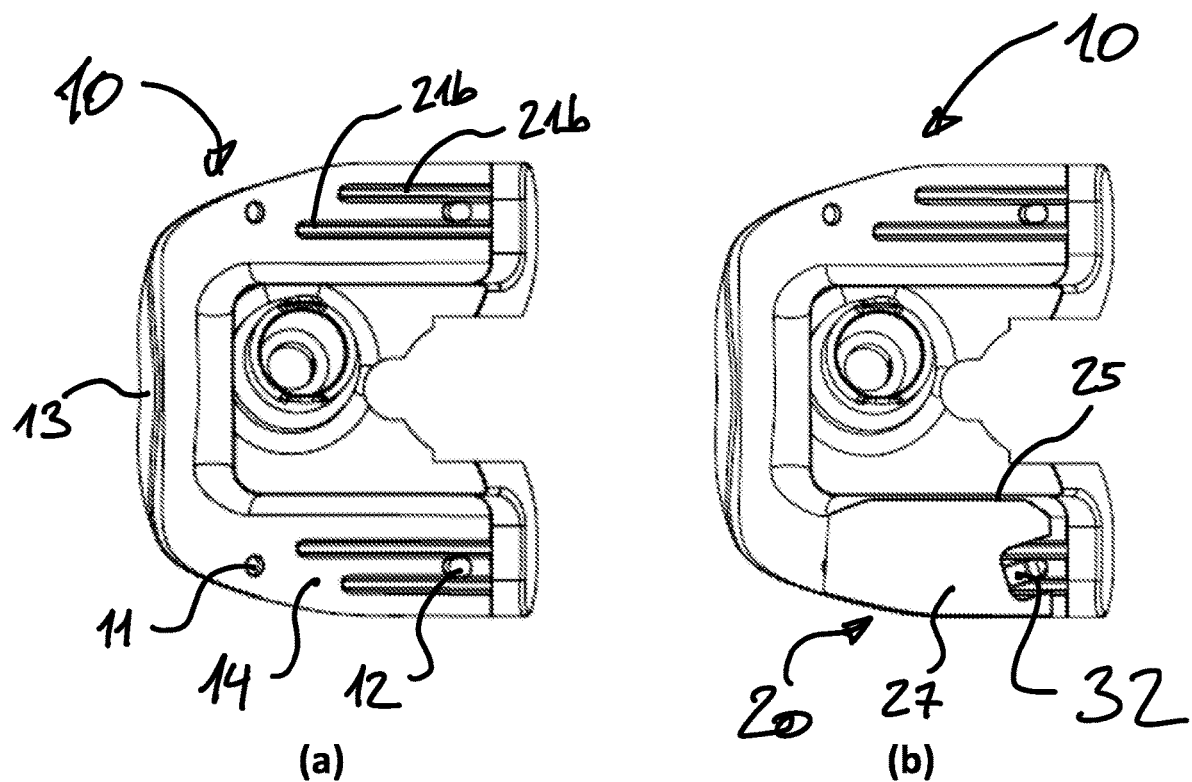
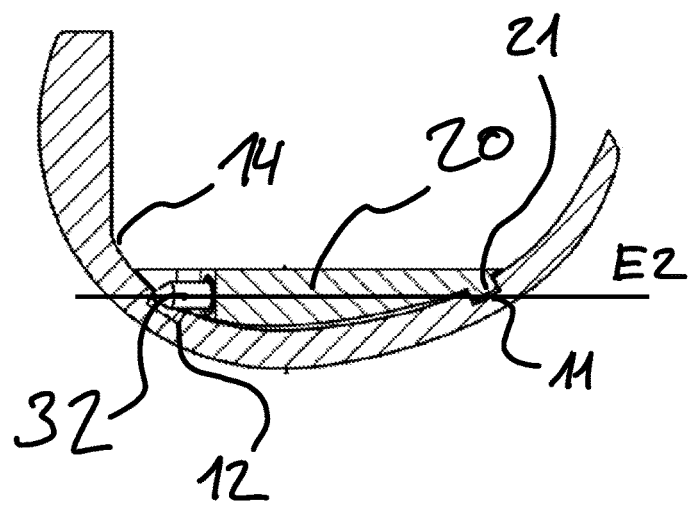
Fig. 3
Fig. 4

INTERMEDIATE SEGMENT FOR A JOINT COMPONENT

CROSS-REFERENCE TO RELATED APPLICATIONS

This application is the National Stage entry under 35 U.S.C. § 371 of International Application No. PCT/EP2017/079301 filed on Nov. 15, 2017, published on May 31, 2018 under Publication Number WO 2018/095778, which claims the benefit of priority under 35 U.S.C. § 119 of German Patent Application Number 10 2016 223 289.4 filed Nov. 24, 2016, the entireties of which are herein incorporated by reference.

FIELD OF THE INVENTION

The invention relates to an intermediate segment for arrangement between a concave implantation surface of a joint component and bone tissue to replace the missing tissue to support the prosthesis. In addition, the invention relates to a joint component with an intermediate segment and a method for securing an intermediate segment to a joint component.

PRIOR ART

When implanting an artificial joint replacement, it is possible that more of a patient's bone stock has to be removed or is already missing than is required for correct fitting of a joint component of the joint replacement. As a result, a space exists in such a situation at least in sections between the joint component and bone tissue. The cause of this may be pre-existing damage to the bone tissue resulting, for example, from a fracture, tumour or necrosis. The result is that the side or surface of the joint component intended for securing the joint component to the bone tissue can no longer be arranged optimally across the entire extension thereof in relation to the bone tissue.

If the side of the joint component facing the bone tissue is a convex side, as is the case with a joint socket of a hip replacement joint, for example, it is possible to build up bone tissue before or even during implantation and still achieve a stable anchorage relatively quickly. Put simply, excessive erosion of the bone tissue can be filled prior to implantation and then "sealed" with the joint component. It is advantageous with this arrangement that the supply of bone tissue is better compared to a scenario where a concave implantation side of a joint component surrounds the bone tissue, at least in part, after implantation. The bone supply will be impaired in the latter case. In addition, in the case of partial surrounding, the bone can be open to the outside, necessitating additional measures to contain the material used to cushion the bone. As an alternative, the aforementioned spaces are therefore often simply filled with bone cement. As a result, using ingrown bone to secure the joint component is no longer possible. Even if the intention from the outset was to use bone cement to anchor the joint component, the area to be filled results in the volume of bone cement required to fill this area being significantly larger in some cases. This presents the risk that the surrounding bone tissue will be exposed to a comparatively higher temperature and will also be exposed to this temperature over a prolonged period of time. As the extent of missing bone tissue can usually only be assessed during the operation, a joint component individually tailored to the patient is not a good and also an extremely costly alternative.

The object of the present invention was therefore to provide a possibility with which a joint component can be adapted to the bone stock available in the individual patient in the scenarios described above, without further damaging the bone tissue.

SUMMARY OF INVENTION

By way of a solution, the present invention proposes an intermediate segment for arrangement between a concave implantation surface of a joint component, particularly a joint prosthesis and preferably a femoral prosthesis, and the bone tissue. The intermediate segment has an intermediate segment body with at least a side facing the joint component, wherein one of the at least one side facing the joint component, particularly the joint prosthesis, is convex, and a locking mechanism for attaching the intermediate segment to the joint component, particularly the joint prosthesis, with at least a first and a second latching element, wherein at least one of the latching elements is movable.

The intermediate segment is a part that is separate to the joint component, but which can be locked onto the joint component mechanically via the latching elements and preferably via a positive-locking fit. The advantage of this is that the best fitting intermediate segment can be selected from a supply of different intermediate segments provided, in order to adapt the joint component to the implantation site. It is possible to make this adjustment during surgery, which means that adjustments are possible right up to the moment just before implantation of the joint component.

Locking occurs by engaging the at least one movable latching element with the joint component. Once all latching elements have engaged, the intermediate segment is firmly attached or locked to the joint component.

In a particularly preferred embodiment, the at least one movable latching element on the intermediate segment can be moved between a release position and a locked position, wherein the movable latching element preferably protrudes from the intermediate segment body in the locked position.

In this embodiment, the engagement of the movable latching element is reversible, which means that the intermediate segment can be detached from the joint component again if necessary. This embodiment therefore advantageously supports modular use of the intermediate segments as well.

The embodiment wherein the movable latching element protrudes from the intermediate segment body in the locked position is particularly advantageous here from a design perspective. Such intermediate segments can thus easily be used in a wide range of joint components and pre-existing joint components. In the case of pre-existing joint components, only a preferably complementary recess into which the latching element can engage must be created in order to be able to attach intermediate segments to such a joint component. A further advantage when preparing the implantation site is that, without an intermediate segment, a recess does not have to be made in the bone surface intended for contact with the joint component.

In another particularly preferred embodiment, at least one of the latching elements is a fixed latching element, wherein the fixed latching element preferably protrudes from the intermediate segment body.

This embodiment allows particularly simple locking of an intermediate segment to the joint component, wherein first the fixed latching element and then the movable latching element are brought into engagement with the joint component by adopting a locked position. In the case of a protruding fixed latching element, the same advantages as those cited in relation to the previous embodiment are achieved. Furthermore, the fixed latching element is formed with the intermediate segment body, preferably integrally or as a single piece, and therefore has high structural strength.

In a further embodiment of the intermediate segment, the intermediate segment body has at least an anchoring surface for attaching the intermediate segment body to the bone tissue. The anchoring surface preferably has a surface structure and/or a coating that is more conducive to ingrowth of bone tissue.

With this embodiment, an anchoring surface of the intermediate segment body is configured, preferably through its surface properties, to provide the best possible conditions for connecting to a patient's bone tissue. This may be a polished surface, for example, to create a connection through the bone cement. In addition, the anchoring surface, with either a rough or porous surface, can enable the joint component to be anchored through ingrowth of bone tissue.

Through the connection with the bone tissue, the intermediate segment then, particularly with this embodiment, becomes a structurally and functionally integral part of the joint component. Furthermore, a surface structure and/or coating can also be beneficial for the use of bone cement, as it increases the contact surface with the bone cement, thereby improving the dissipation of heat.

In another particularly preferred embodiment, the first latching element has a first engagement axis and the second latching element has a second engagement axis, wherein the angle between the first engagement axis and the second engagement axis is different from zero.

Due to the fact that the engagement axes of the at least two latching elements are arranged at an angle to each other, the engagement of these latching elements creates a positive-locking fit of the intermediate segment with the joint component. An engagement axis is understood to mean the axis along which a latching element is moved in order to engage with an opposite, preferably complementary engagement element of the joint component and thus preferably create a positive-locking fit between the intermediate segment and the joint component. In addition, the engagement axes of the latching elements preferably move apart starting from the intermediate segment body.

In a particularly preferred embodiment, the latching elements are arranged on the convex side of the intermediate segment in order to interact with the joint component.

An arrangement of this kind is particularly advantageous in terms of the joint force running through the artificial joint, as this force presses the intermediate segment and joint component together and the latching elements or engagement elements are therefore only exposed to minimal load, if any. Since, parallel to the joint surfaces, only minimal forces caused by the joint friction are transmitted, any shear load on the connection between the intermediate segment and joint segment can also be kept small.

In another particularly preferred embodiment, the movable latching element of the intermediate segment is designed as a pin. This pin has a locking section in its longitudinal direction on one side and preferably a tool engagement section on the other opposite side. A threaded pin is a particularly preferred design for the pin.

The movable latching element designed as a pin is preferably movable in the longitudinal direction of the pin between the release position and the locked position. This movable latching element can be actuated using the tool engagement section. The movement of the movable latching element upon actuation preferably takes place by means of a threaded engagement between the latching element and intermediate segment body. To put it more specifically, the pin moves as a result of being rotated by means of the tool engagement section. This rotation is converted into a longitudinal movement through the thread of this pin. A movable latching element of this kind has a particularly simple and robust design. In addition, the thread can be self-locking such that the movable latching element cannot work loose by itself.

In a particularly preferred embodiment of the intermediate segment, the tool engagement section of the movable latching element designed as a pin is accessible from a free side of the intermediate segment body for movement of the pin.

A free side in this context is understood to mean a side of the intermediate segment body that does not abut the bone tissue or that is not facing the joint component when the joint component is implanted. Such a design for the intermediate segment is particularly beneficial in the case of a revision of the joint component, as part of the joint component is already separated from the bone tissue as a result of a release of the locking of the intermediate segment, thereby making it easier to remove the joint component. The intermediate segment can be either reused or removed after a replacement of the joint component, wherein if the segment is removed, very easy access to the intermediate segment is created as a result of the prior removal of the joint component.

In another preferred embodiment, the intermediate segment body comprises a visibility section preferably designed as a recess.

This visibility section makes it easier for the intermediate segment to be locked to the joint component and is preferably arranged on the side of the movable latching element so that the engagement of the movable latching element with an engagement element of the joint component can be observed and monitored during assembly of the intermediate segment. In other words, the engagement movement in the joint component in the case, for example, of a latching element moving out of the intermediate segment body into a locked position can be seen through the visibility section. Assembly and checking the locked state are therefore considerably easier in this embodiment.

In addition, the present invention provides a joint component and preferably a femoral component. This joint component has a concave implantation surface with an intermediate segment that can be secured to the joint component via a locking mechanism. The intermediate segment has a convex side that is facing the concave implantation surface of the joint component when the intermediate segment is secured and locked.

With this combination of a joint component and intermediate segment, the aforementioned advantages for implantation and revision of the joint component on a patient's bone tissue can be achieved.

In a particularly preferred embodiment, the joint component has at least two engagement elements, wherein the engagement elements are arranged on at least one side facing the intermediate segment, preferably the concave implantation surface.

The engagement elements of the joint component are preferably designed to be complementary to the latching elements of the intermediate segment, at least in part. As already mentioned above, the engagement elements are preferably designed as recesses for the joint component.

In another preferred embodiment, the intermediate segment can be secured to the joint component by means of a positive-locking fit.

In other words, with this embodiment the intermediate segment is locked to the joint component by means of an engagement of the latching elements and in particular by means of the at least one movable latching element, so that the latching elements prevent a relative movement between the intermediate segment and the joint component. The advantages of this type of connection are firstly that it is detachable and secondly that it is not dependent on friction between the intermediate segment and joint component, as would be the case with locking by means of a friction fit.

Furthermore, the present invention provides a method for securing an intermediate segment to a concave implantation surface of a joint component, wherein the method comprises the following steps. To assemble the intermediate segment on the joint component, a first latching element of the intermediate segment is brought into engagement with a first engagement element of the joint element. In addition, a second latching element of the intermediate segment is brought into engagement with a second engagement element of the joint component. At least one of the latching elements of the intermediate segment is a movable latching element and the engagement axes of the latching elements form an angle different from zero.

This method allows a joint component to easily be adapted to the implantation site in a modular manner prior to implantation as already described in connection with the intermediate segment.

In a particularly preferred embodiment, the engagement between the latching elements of the intermediate segment and the engagement elements of the joint component is effected by means of a positive-locking fit on the concave implantation surface of the joint component in order to achieve the aforementioned advantages when securing the intermediate segment to the joint component.

BRIEF DESCRIPTION OF THE FIGURES

The figures below illustrate preferred embodiments of the present invention. However, they are not intended to restrict the scope of protection of the claims, but are merely intended, together with the description below, to facilitate easier understanding of the invention. In the figures, the same reference numerals refer to features that have the same or an equivalent function and/or structure. The figures show embodiments of the intermediate segment and joint component as follows:

FIG. 1 is a three-dimensional schematic view of a joint component to which an intermediate segment can be secured.

FIG. 2a is a three-dimensional schematic view of an intermediate segment as seen from the side that is facing the joint component when the intermediate segment is locked.

FIG. 2b shows a three-dimensional schematic view of an intermediate segment as seen from the side that is facing the bone tissue of the implantation site when the intermediate segment is locked.

FIG. 3a shows the joint component of FIG. 1 as seen from the implantation side.

FIG. 3b corresponds to the view in FIG. 3a with an implanted intermediate segment on the concave surface of the joint component.

FIG. 4 is a sectional view along line A-A of FIG. 3b.

DETAILED DESCRIPTION OF PREFERRED EMBODIMENTS

The exemplary embodiment illustrated in FIG. 1 has the femoral component of a knee endoprosthesis as joint component 10. The intermediate segment of the invention can of course also be used on other joint components that have a concave implantation surface.

The distal end of the exemplary joint component 10 shown in FIG. 1 is provided with a convex joint surface 13 that faces the joint surface of a second joint component when the joint replacement is implanted.

The side of the joint component 10 opposite the joint surface 13 is provided with a concave implantation surface 14. This concave implantation surface 14 faces the patient's bone tissue when the joint component 10 is implanted.

Normally, the concave implantation surface 14 can be positioned in relation to the bone tissue of an implantation site such that an optimal connection with the neighbouring bone tissue can be achieved. This means that when the joint component 10 is anchored with bone cement, for example, the bone tissue is located at a predetermined distance from the implantation surface 14 such that the bone cement being used for securing can create a connection between the concave implantation surface 14 and the bone tissue. If the joint component 10 is intended to be anchored by means of ingrown bone tissue, the bone tissue of the prepared implantation site sits as directly as possible on the concave implantation surface 14 during implantation.

As explained above, however, there are situations in which positioning of the concave implantation surface 14 in relation to the patient's bone tissue for optimum anchoring of the joint component 10 is not possible due to insufficient bone tissue. For this reason, the joint component 10 in FIG. 1 is provided with a first engagement element 11 and a second engagement element 12.

In the exemplary embodiment, a first latching element 21 and a second latching element 32 engage in these engagement elements 11, 12 in order to secure an intermediate segment 20 to the joint component 10 (see FIG. 4). In addition to at least two latching elements 11, 12, an intermediate segment 20 of the invention particularly comprises an intermediate segment body 23.

As illustrated in FIGS. 2a and 2b, a convex side 24 corresponding to the concave implantation surface 14 of the joint component 10 is formed on the intermediate segment body 23 of the intermediate segment 20. As can be seen in FIG. 4, the convex side 24 of the intermediate segment 20 is preferably intended to abut the concave implantation surface 14 of the joint component 10. It should be noted in this context that the larger the abutting surface of the convex side 24 of the intermediate segment body 23, the better the transmission of joint forces via the intermediate segment 20 arranged between the bone tissue and the joint component 10. The entire convex side 24 of the intermediate segment body 23 facing the concave implantation surface 14 therefore preferably abuts the implantation surface 14. The convex side of the intermediate segment body 23 and/or the concave implantation surface 14 of the joint component 10 may have a bent and/or faceted profile.

In addition, the intermediate segment body 23 may, as shown in the exemplary embodiment of FIGS. 2a and 2b, comprise another side 25 facing the joint component 10. When installed, this is opposite the side 15 of the joint component 10 (see FIG. 1). A third side 26 of the intermediate segment body 23 facing the joint component 10 is described in more detail below.

The latching elements 21, 32 are arranged on at least one of sides 24, 25, 26 of the intermediate segment 20; these sides are all facing the joint component 10. This enables the latching elements 21, 32 to be engaged with the joint body 10. In the exemplary embodiment illustrated in FIG. 2, a fixed latching element 21 is arranged on the convex side 24 of the intermediate segment body 23 and a movable latching element 32 is arranged on the third side 26 of the intermediate segment body 23 facing the joint component 10. However, an arrangement of the latching elements 21, 32 of the intermediate segment on another side facing the joint component 10 is also possible. It is therefore conceivable in relation to FIG. 1 that a latching element 21, 32 of the intermediate segment 20 can be engaged with a corresponding engagement element 11, 12 on the side 15 of the joint component 10.

As shown in the exemplary embodiment of the intermediate segment 20 shown in the figures, the fixed latching element 21 is preferably designed as a protrusion. The same applies to the movable latching element 32.

The fixed first latching element 21 can also be designed as an integral part of the intermediate segment body 23, as shown in FIGS. 2a and 4. The advantage of this is that it has a particularly high structural strength. In addition, the fixed latching element 21 of this exemplary embodiment shown in FIG. 2a is designed as a cylinder. This cylinder has an engagement axis E1 via which the fixed latching element 21 of the intermediate segment 20 can be engaged with the engagement element 11 of the joint component 10.

It is understandable that the latching element 21 can have any shape, provided that it enables engagement with the joint component 10. It is possible, for example, to provide one edge of the intermediate segment body 23, such as the edge denoted by reference numeral 21a in FIG. 2a, for engagement with the joint component 10. Such an engagement edge 21a could engage with a corresponding recess in the concave implantation surface 14.

A latching element can also be designed as a groove or an elongated protrusion. Grooves with such a function can, for example, be designed in the same way as the grooves 21b designed in the implantation surface 14. However, it should be pointed out that the grooves 21b do not have this kind of function in the embodiment illustrated. This is easy to see on the convex side 24 of the intermediate segment body 23, as it does not have any corresponding latching elements. In addition, the first latching element 21 can be designed as a movable latching element in the same way as the second latching element 32.

Furthermore, the intermediate segment 20 comprises a movable latching element 32 that can be engaged with the second engagement element 12 of the joint component 10. The movable latching element 32 is designed as a pin in the preferred embodiment of the intermediate segment 20 shown here. The movable latching element 32 has a locking section in its longitudinal direction on one of its ends and preferably a tool engagement section, not shown, on the opposite end. As can be seen in the exemplary embodiment shown in FIGS. 3b and 4, the locking section can be designed so that it is tapered and in particular conical to facilitate engagement in the engagement element 12.

The movable latching element 32 can be moved along a second engagement axis E2 from a release position to a locked position. In the locked position, the latching element 32 engages with the engagement element 12 of the joint component 10 as shown in FIG. 4. The movement of the latching element 32 in the illustrated exemplary embodiment is enabled by a thread engagement not shown. To this end, the latching element 32 has an external thread (not shown). This external thread engages with an internal thread provided in a through hole 22 of the intermediate segment body 23. As shown in FIG. 2, an opening of the through hole 22 is preferably located on a free side 28 of the intermediate segment body 23. This enables a tool to engage with the tool engagement section of the latching element 32 via this opening even when the joint component 10 has already been implanted. This particularly has the advantages described above in relation to a revision operation.

In the exemplary embodiment shown in FIG. 2, the second opening of the through hole 22 is located in the third side 26 of the intermediate segment body 23 facing the joint component 10. The third side 26 of the intermediate segment body 23 forms a recess 29 through which an engagement of the movable latching element 32 with the corresponding engagement element 12 of the joint component 10 can be observed and monitored (see also FIG. 3b).

In addition, the side of the intermediate segment body 23 facing the bone tissue when implanted can also be designed as an anchoring surface 27. The anchoring surface 27 is provided with a surface that is conducive to the formation of an anchorage or connection of the bone tissue with the intermediate segment 20 and therefore the joint component 10, depending on the anchoring technique used. Anchoring techniques suitable for implantation particularly include a connection via bone cement or anchoring via the ingrowth of bone into the surface of the implant. Consequently, due to the designs of anchoring surface 27 described above, the intermediate segment can support anchoring of the joint component 10 and thus perform the function of the implantation surface.

To assemble an intermediate segment 20 on a joint component 10, an intermediate segment 20 with an intermediate segment body 23 that allows the best possible adaptation of the geometry of the joint component 10 to the implantation site is first selected. In other words, the intermediate segment body 23 can replace the missing bone tissue in the best-case scenario.

The selected intermediate segment 20 is then brought into engagement with the first engagement element 11 or second engagement element 12 of the concave implantation surface 14 via the at least two latching elements 21, 22 and thus locked onto the joint component 10.

In the exemplary embodiment of an intermediate segment 20 shown in FIG. 2, locking of the intermediate segment 20 to the joint component 10 occurs by first bringing the fixed latching element 21 into engagement with the corresponding engagement element 11 on the concave implantation surface 14 of the joint component 10. Engagement takes place along a first engagement axis E1.

The next step is that the movable latching element 32 is then brought into engagement with the second engagement element 12 along a second engagement axis E2. In the case of the exemplary embodiment, this is done by inserting a tool into the through hole 22 and engaging the tool tip with a tool engagement section of the movable latching element 32.

In the embodiment illustrated in the figures, the latching element 32 designed as a pin is rotated around its longitudinal axis via the tool so that it can be moved by means of an engagement of its thread with the intermediate segment body 23 in its longitudinal direction between a release position, where the intermediate segment 20 can be detached from the joint component 10, and a locked position, where the intermediate segment can be locked with the joint component. In addition, the thread can be designed as a self-locking thread so that the movable latching element cannot unintentionally move from the locked position to the release position.

This movement of the latching element 32 thus enabled between a release position and a locked position will preferably be visible to the user via a visibility section formed by a recess 29, which in turn is formed at least in part by the side 26, so that a correct locking can be ensured.

Instead of the latching element 32 being designed as a pin, it can also be designed in the form of a hook and be engaged with the joint component 10 by means of a rotary movement.

Regardless of the mechanism by means of which the movable latching element 32 engages, locking of the intermediate segment 20 onto the joint component 10 occurs preferably by means of a positive-locking fit. In other words, the latching elements 21, 32 can be brought into engagement with the engagement elements 11, 12 of the joint component 10 so that the intermediate segment 23 is locked onto the joint component 10. When locked, the latching elements 21, 32 and engagement elements 11, 12 are engaged such that the intermediate segment 20 can no longer be detached from the joint component 10 in any direction. In other words, when locked, the intermediate segment 20 does not have any degree of freedom in relation to the joint component 10.

In particular with a positive-locking fit, the intermediate segment is preferably made from metal in order to provide a high-strength lock.

The intermediate segment of the present invention thus provides a solution that is cost effective and easy to operate, by means of which a joint component 10 can be reliably anchored to bone tissue, even if the amount of available bone tissue is insufficient, and which at the same time prevents further damage to the bone tissue.

REFERENCE NUMERALS

10 Joint component
11 First engagement element
12 Second engagement element
13 Convex joint surface
14 Concave implantation surface
15 Side facing the intermediate segment
20 Intermediate segment
21 First latching element (fixed latching element)
21a Edge usable as a latching element
21b Groove or protrusion usable as a latching element
22 Through hole with internal thread
23 Intermediate segment body
24 First side facing the joint component (convex side)
25 Second side facing the joint component
26 Third side facing the joint component
27 Anchoring surface
28 Free side of the intermediate segment body
29 Recess on intermediate segment body
32 Second latching element (movable latching element)
E1 First engagement axis
E2 Second engagement axis

The invention claimed is:

1. An intermediate segment for arrangement between a concave implantation surface of a joint component, and bone tissue, wherein the intermediate segment comprises:
an intermediate segment body comprising at least one side facing the joint component, an anchoring surface opposite the at least one side facing the joint component, a second side substantially perpendicular to both the anchoring surface and the at least one side facing the joint component, and a free side opposite the second side, wherein one of the at least one side facing the joint component is convex, and
a locking mechanism for attaching the intermediate segment to the joint component in which the intermediate segment has at least a first latching element and a second latching element, wherein at least one of the first latching element and the second latching element is a movable latching element and at least one of the first latching element and the second latching element is a fixed latching element,
wherein the fixed latching element is an integral part of the intermediate segment body,
wherein the first latching element and the second latching element do not contact each other,
wherein the second latching element is the movable latching element and the second latching element has a second engagement axis, and
wherein the second engagement axis extends through a portion of the free side.

2. The intermediate segment of claim 1, wherein the movable latching element can be moved between a release position and a locked position and wherein the movable latching element protrudes from the intermediate segment body in the locked position.

3. The intermediate segment of claim 1 wherein the locking mechanism comprises one fixed latching element, and wherein the fixed latching element protrudes from the intermediate segment body.

4. The intermediate segment of claim 1, wherein the intermediate segment body comprises an anchoring surface configured to attach to bone tissue, wherein the anchoring surface has a surface structure and/or coating that is configured for ingrowth of bone tissue.

5. The intermediate segment of claim 1, wherein the first latching element has a first engagement axis and, wherein the angle between the first engagement axis and the second engagement axis is different from zero.

6. The intermediate segment of claim 1 wherein the first latching element and the second latching element are arranged on the convex side of the intermediate segment in order to interact with the joint component.

7. The intermediate segment of claim 1, wherein the movable latching element is designed as a pin that has a locking section in its longitudinal direction on one side and a tool engagement section on the other opposite side.

8. The intermediate segment of claim 7, wherein the tool engagement section of the pin is accessible from a free side of the intermediate segment body for movement of the pin.

9. The intermediate segment of claim 7 wherein the movable latching element is designed as a threaded pin.

10. The intermediate segment of claim 1, wherein the intermediate segment body has a visibility section designed as a recess.

11. The intermediate segment of claim 1, wherein the first latching element is the fixed latching element, and wherein the fixed latching element is cylindrical.

12. The intermediate segment of claim 1, further comprising a third side, wherein the third side forms a recess.

13. A joint component, comprising:
a concave implantation surface; and
an intermediate segment that can be secured to the joint component by means of a locking mechanism, wherein the intermediate segment comprises at least one side facing the joint component, an anchoring surface opposite the at least one side facing the joint component, a second side substantially perpendicular to both the anchoring surface and the at least one side facing the joint component, and a free side opposite the second side, wherein one of the at least one side facing the joint component is convex, and
wherein the joint component comprises at least two engagement elements that each engage with a first latching element and a second latching element of the intermediate segment, wherein the first latching element and the second latching element of the intermediate segment do not contact each other, wherein the second latching element is a movable latching element and the second latching element has a second engagement axis, and wherein the second engagement axis extends through a portion of the free side.

14. The joint component of claim 13, wherein the engagement elements are arranged on at least one side facing the intermediate segment.

15. The joint component of claim 14, in which the engagement elements are arranged on the concave implantation surface.

16. The joint component of claim 13, wherein the intermediate segment can be secured to the joint component by means of a positive-locking fit.

17. The joint component of claim 13, in which the joint component is a femoral component.

18. The joint component of claim 13, wherein the first latching element is the fixed latching element, and wherein the fixed latching element is cylindrical.

19. The joint component of claim 13, wherein the intermediate segment further comprises a third side, wherein the third side forms a recess.

* * * * *